United States Patent [19]

Jordan et al.

[11] Patent Number: 4,816,226
[45] Date of Patent: Mar. 28, 1989

[54] APPARATUS FOR CONTINUOUS FLOW INJECTION SOLVENT EXTRACTION ANALYSIS

[75] Inventors: Jeffrey W. Jordan, Katy; Don C. Olson, Houston, both of Tex.

[73] Assignee: Shell Oil Company, Houston, Tex.

[21] Appl. No.: 139,876

[22] Filed: Dec. 30, 1987

[51] Int. Cl.⁴ ............................................. G01N 33/00
[52] U.S. Cl. .......................................... 422/81; 422/68
[58] Field of Search ................. 422/68, 81, 82, 64; 436/52, 53, 111, 150

[56] References Cited

U.S. PATENT DOCUMENTS

| | | | |
|---|---|---|---|
| 3,572,994 | 3/1971 | Hochstrasser | 23/230 |
| 3,615,227 | 10/1971 | Molndal et al. | 23/230 |
| 3,743,103 | 7/1973 | Isreeli et al. | 210/532 |
| 3,921,439 | 11/1975 | Burns | 73/61 R |
| 4,013,413 | 3/1977 | Stewart et al. | 422/81 |
| 4,022,575 | 5/1977 | Hansen et al. | 422/81 |
| 4,272,483 | 6/1981 | Schick | 422/67 |
| 4,312,635 | 1/1982 | Carlisle | 422/81 |

Primary Examiner—Barry S. Richman
Assistant Examiner—T. J. Wallen
Attorney, Agent, or Firm—Ronald R. Reper

[57] ABSTRACT

An analytical system is disclosed employing dual valve injector sampling and suitable for continuous flow injection analysis employing extraction of a liquid sample with an immiscible liquid solvent for a component of said sample liquid.

8 Claims, 1 Drawing Sheet

APPARATUS FOR CONTINUOUS FLOW INJECTION SOLVENT EXTRACTION ANALYSIS

BACKGROUND OF THE INVENTION

The present invention relates to an analytical system for continuous flow analysis employing flow injection solvent extraction. Continuous flow analytical systems in which there is provided a continuous unobstructed carrier stream into which discrete volumes of sample solutions to be observed for reaction with the carrier stream are injected successively are known and described, e.g., in U.S Pat. No. 4,013,413 and 4,022,575, the specifications of each being incorporated herein by reference. However, the systems described therein have drawbacks when applied to solvent extraction analysis in the requiring the use of segmenters and/or phase separators and the like. Such segmenters/phase separators typically need frequent maintenance and adjustment for continuing reliable results. The need for such adjustments has been an obstacle in the development of a system capable of continuous fully automated operation for analytical procedures involving extraction of a liquid sample with an immiscible solvent.

SUMMARY OF THE INVENTION

An object of the present invention is to provide an analytical system for analysis by flow injection and solvent extraction in which the use of segmenters and phase separators may be avoided, and which system can be fully automated by the use of injector valves actuated in sequence by, e.g., a conventional sequence programmer or a timer in combination with a suitable detection device to capture a precise portion of the injected solvent for measurement in a separate flow system.

The analytical system according to the invention comprises apparatus for measuring a property of a first liquid by extracting a component thereof from said first liquid into a second liquid which is a solvent for a component of said first liquid and is immiscible with said first liquid, separating a portion of said second liquid, and measuring a property of the component extracted into said second liquid, which apparatus comprises:

(a) first means for supplying, for supplying said first liquid from a source thereof to a first liquid flow system and at a substantially constant flow rate when said apparatus is in operation;

(b) said first liquid flow system comprising (1) a first multiport valve injector having a plurality of ports including a first inlet port in fluid communication with said first means for supplying, and a first outlet port in interruptible flow communication with said first inlet port and provided with fluid channels adapted to register with the aforesaid ports to control the flow of fluid through each said port, (2) extraction means for partitioning of a component from said first liquid into said second liquid and comprising capillary tubing configured to enhance mixing within the liquids passing therethrough; said tubing having two ends, an upstream end in flow communication with said first outlet port on said first valve injector and serving as an inlet, and a downstream end serving as an outlet, (3) a second multiport valve injector having a plurality of ports including a first inlet port in flow communication with said outlet end of said extraction means and having a first outlet port in interruptible flow communication with said first inlet port and serving as an outlet of said first liquid flow system, having liquid channels adapted to register with the aforesaid multiports to control the flow of liquid through each said port, and provided with means for injecting a fixed volume of the flow therethrough into said second liquid flow system;

(c) means for supplying a second liquid (immiscible with said first liquid) from a source thereof into all or part of said second liquid flow system and at a substantially constant flow rate when said apparatus is in operation;

(d) said second liquid flow system comprising: (1) said second multiport valve injector having a second inlet port operatively connected via conduit means, directly or indirectly, to said means for supplying second liquid; having a second outlet port for passing said second liquid flow via conduit means downstream to property measurement means, and having flow injection means for discontinuously capturing a portion of substantially only said injected segment of second liquid from said first liquid flow system and injecting said portion into said second liquid flow system; and (2) said first multiport valve injector having a second inlet port operatively connected directly or indirectly to means for supplying second liquid; having a second outlet port for passing said second liquid flow; and having flow injection means for discontinuously injecting a segment of said second liquid into said first flow system upstream of said extraction means;

(e) property measurement means operatively coupled to said second liquid flow system downstream of said second valve injector, for measuring the desired property of the liquid flowing in said second liquid flow system; and (f) timing means operatively coupled to sid first valve injector to timely operate said first valve injector to periodically inject a segment of said second liquid into said first liquid flow system, and (g) activating means to timely operate said second valve injector to capture a portion of said segment of second liquid from said first liquid flow system after contact with the first liquid in said extraction means, and to inject said captured portion into said second fluid flow system.

In an alternate embodiment the second flow system consists of two subsystems each having separate supply means; the composition of the second liquid supplied to each subsystem may differ, but must be mutually miscible. If desired, said second fluid may include an operatively effective amount of a component such as, e.g., a chemical indicator and/or reagent in one or both subsystems.

BRIEF DESCRIPTION OF THE DRAWINGS

FIG. I is a schematic representation of a preferred embodiment of the system and apparatus of the present invention wherein the second liquid flow system is supplied by a single supply means.

FIG. II is a schematic representation of an embodiment of the system and apparatus of the invention wherein the second liquid flow system consists of two separately supplied subsystems.

DESCRIPTION OF PREFERRED EMBODIMENTS

Figure 1:
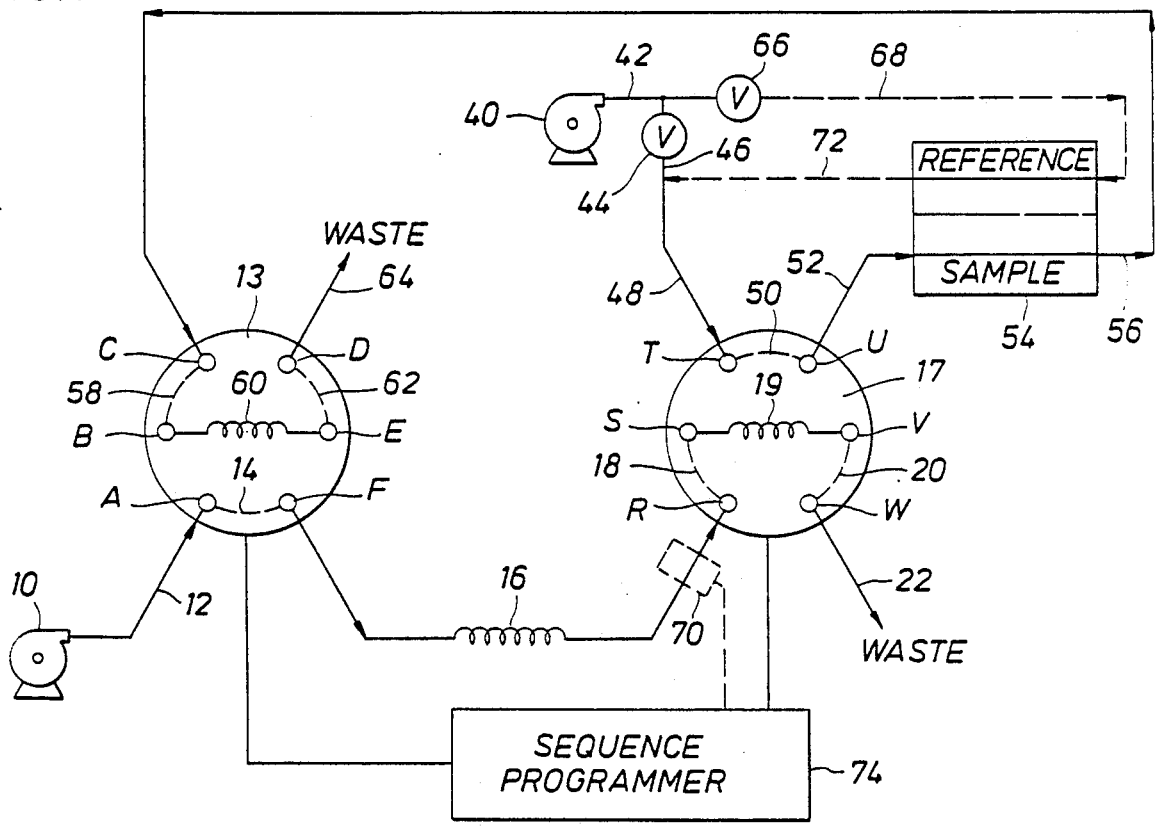

The invention will now be described in more detail by way of example with reference to FIG. 1 illustrating a preferred embodiment, and which shows that it is comprised of a separate flow system for each of a first liquid and a second liquid, said second liquid being immiscible with said first liquid. The two liquid flow systems have but two elements in common, namely first valve injector 13, and second valve injector 17.

The first fluid flow system comprises first supply means including constant flow rate pump 10, connected to a source of first fluid when operating (not shown), and supply conduit 12 in flow communication with inlet port A of first valve injector 13 and thence in interruptible flow communication via valve internal channel 14, to outlet port F. In said first fluid flow system, port F of said first injector valve 13 is operatively connected to the inlet (upstream) end of extraction means 16 such as a capillary tube configured to enhance mixing within the segment of injected fluid passing therethrough, and most preferably in the shape of a coil, as shown. The capillary tube outlet (downstream) end is in flow communication with inlet port R on second valve injector 17 whence fluid in said first fluid system normally flows via internal channel 18 to port S thence via loop 19, port V, internal channel 20 to outlet port W and thence via conduit 22 to waste.

The second liquid flow system comprises second supply means such as constant flow rate pump 40 operatively connected to a source of second liquid when operating (not shown), to discharge into conduit 42 to provide said second fluid, which is immiscible with said first liquid, and to flow via optional valve 44 and conduits 46 and 48 to inlet port T of second valve injector 17, thence normally via internal channel 50, port U and conduit 52 operatively coupled with property measurement means 54, which preferably is a flow through detector. From property measurement means 54 the second liquid flow system further comprises conduit 56 to carry the flow of second liquid to inlet port C on first valve injector 13 and thence via internal channel 58, port B, loop 60, port E and internal channel 62 to outlet port D. From outlet port D the second liquid flow system further comprises conduit 64 to carry the flow of second fluid to waste.

Property measurement means 54 may be any type of analytical detector known and desired for a particular analysis; detection techniques suitably employed according to the invention are well known in instrumental analysis and include flame photometry, spectrophotometry, nephelometry, fluorescence, chemiluminescence, voltametry, potentiometry with ion selective electrodes, and atomic absorption spectrophotometric and the like. Ordinarily the property measurement means, also referred to herein as a detector will be operatively coupled to readout devise (not shown) such as a recorder or microcomputer having a display screen.

In a preferred embodiment the property measurement means 54 is also operatively connected to the flow of the second liquid prior to extraction means 16 as well as after said means in order to provide a "blank" sample for the property to be measured. In this manner the property to be measured in the second liquid can be determined both before and after extraction with the immiscible liquid and compared to better determine the influence of the component extracted from the first liquid into the second liquid. This is shown in FIG. 1 wherein at least a portion, and preferably all of the second liquid is passed from conduit 42, via optional valve 66, and conduit 68 through optional reference flow cell of property measurement means 54 and is passed via optional conduit 72 and conduit 48 to inlet port T of second valve injector 17. The valve injectors are conventional and commercially available.

Timing means are embodied in sequence programmer 74 operatively connected to first valve injector 13 to intermittantly activate said valve injector to cause the rotation of internal channels 58, 62 and 14 by an arc of 60 degrees and thereby connect inlet port A with port B for a period of time sufficient to cause the desired amount of second liquid which is present in loop 60, to pass via port E thence to port F into the first flow system and thence to extraction means 16; upon inactivation of said first injector valve said internal channels rotate back to the original position as shown in FIG. 1 to resume flow of the first liquid from port A through channel 14 and port F to extraction means 16. In this manner there is an interface of first liquid at each end of the segment of second liquid injected into the first liquid system as well as along the walls of the tubing. The configuration of the capillary tubing causes internal mixing within the segment of second liquid as it passes therethrough. In one embodiment, based upon the flow rate of the first liquid system and the volume of the extraction means, the sequence programmer at a preset time then activates second valve injector 17 to rotate internal passages 18, 50 and 20 by an arc of 60 degrees so as to connect port T via loop 19 with port U to capture a precise portion of the segment of second liquid previously injected into the first liquid flow system and which has passed through the extraction means 16 and to inject said captured portion into the second liquid flow system to pass via conduit 52 to detection means 54.

In an alternate embodiment instead of a sequence programmer operationally connected to both valve injectors, a simple timer (not shown) may be operationally connected to the first valve injector 13 to operate said first valve injector at the desired frequency of injecting the second liquid into the first liquid system, and a suitable detector 70, such as a "plug" detector, based upon appropriate dissimilar liquid detection means, such as a refractive index detector or the like is installed on the outlet end of extraction means 16. This "plug" detector is used to determine the presence of the segment of the second liquid and is operationally connected to a controller such as sequence programmer 74 to operate said second valve injector 17 for a precise time period to capture a precise portion of said segment as it passes through loop 19 of second injector valve 17 as previously described, and to inject said portion of said segment into the second liquid flow system.

In a preferred embodiment, loop 60 in first valve injector valve 13 has a volume larger than the volume of loop 19 in second valve injector 17, for example 1.1 to 10 times the volume of the loop in second injector valve 17, whereby some leeway is provided for timely operation of the second valve injector in relation to operation of the first valve injector and that substantially only the second liquid segment is captured and injected into the second liquid flow system. It has been found that the mixing within each segment of the liquids as they traverse the capillary tube 16 is sufficient to enable extraction of a component from the first liquid with the second liquid at the interface of the liquids in said tube, and that the precise capturing of a like portion of segment of the second liquid is such capturing of only said like portion will suffice for measuring the desired property by means of detection means. Accordingly it is possible to have but a single phase liquid passing through the property measurement means, enabling increased sensitivity and reliability with reduced necessity for maintenance.

Figure 2:
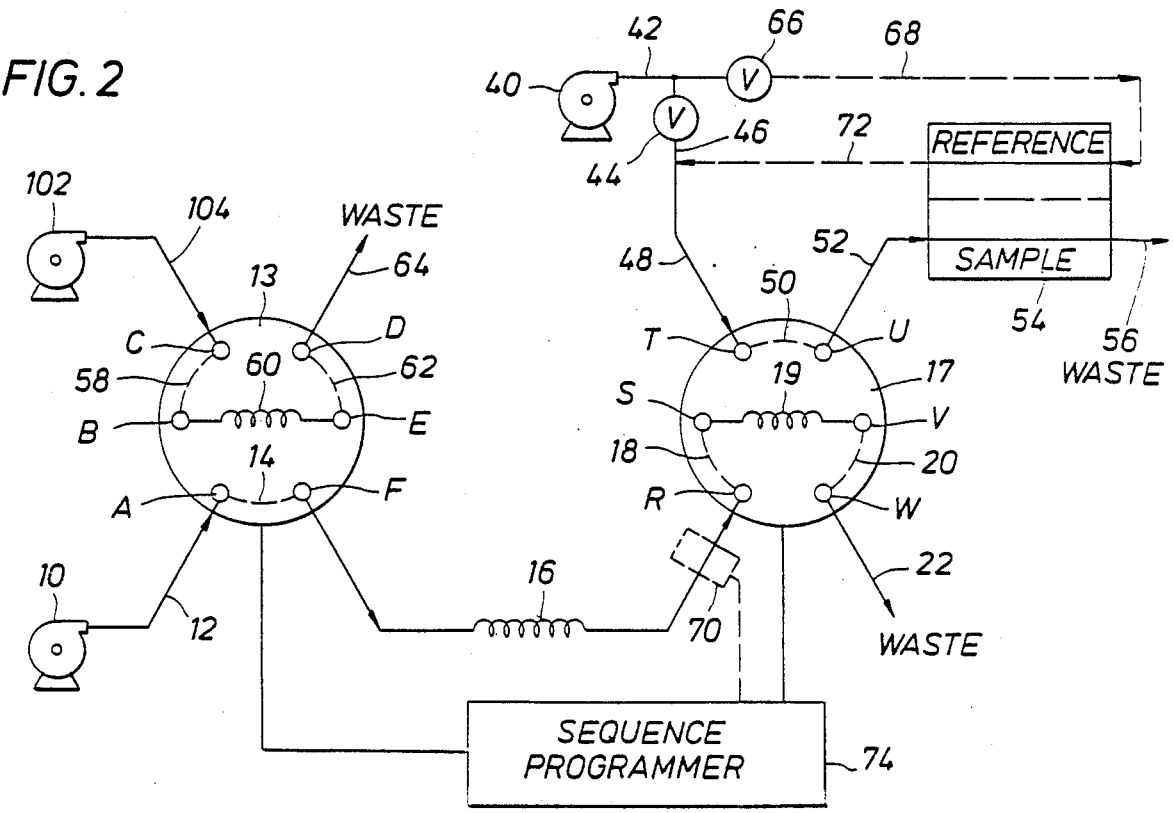

As will be appreciated by those skilled in the art it is possible to use variations on the particular flow path for the second liquid. As shown in FIG. 2, the second liquid flow system may comprise two separate parts, each supplied by separate supply means. In this manner one can use one pump 102 to supply an extractant solvent of one composition, e.g., an alcohol to the first valve injector 13 to extract a component from the material to be analyzed (first fluid), e.g., a hydrocarbon supplied from pump 10, and after flowing through extraction coil 16, capture a portion of the "fat" alcohol segment containing the extractable component of the first liquid, if any, with second valve injector 17 and pass it into indicator and/or reagent-containing aqueous carrier liquid supplied from pump 40 (the water being miscible with the alcohol, but immiscible with the hydrocarbon first liquid). In this instance both the alcohol and water are second liquid within the scope of this invention. It should be noted that identical elements shown in the Figures have been indicated with the same reference numeral. In FIG. 2 the first liquid flow system remains as previously described. The second liquid flow system, comprises two separate parts or subsystems, each having its own supply means such as a precision flow rate pump; the first part comprises second means for supplying 40 connected to a source of second liquid when operating (not shown), and discharging into conduit 42, thence via optional valve 44 and conduits 46 and 48 to inlet port T on second valve injector 17, internal channel 50, outlet port U, thence via conduit 52 through detection means 54 and conduit 56 to waste. The second part of the second liquid flow system comprises third means for supplying 102, which is preferably a constant rate delivery pump connected to a source of second liquid (not shown), which need not have the identical composition as the liquid supplied by second means for supplying 40, but is at least miscible therewith, and discharging into conduit 104, thence inlet port C of first valve injector 13, thence via internal channel 58, port B, loop 60, port E, internal channel 62, port D and conduit 64 to waste.

Although this alternate embodiment will be more costly in requiring an additional supply pump, and will require some additional amount of second liquid to operate on a continuous basis, it is found that this design better avoids the risk of contaminating the second liquid flowing to the detection mean; and may operate with great precision for longer period without requiring frequent adjustment and or maintenance.

Both liquid flow systems, at least the liquid contacting parts thereof, should be made of materials which are inert to the liquids flowing through them; suitable materials for many liquids include, e.g., polypropylene, polychlorotrifluoroethylene (Kel F) and polytetrafluoroethylene (Teflon). Capillary tubing and conduits having internal diameter from about 0.1 mm to about 2 mm are suitable for use in the invention.

For the purpose of this invention the valve injectors may be of any type of valve injectors known, e.g., pneumatic, electrical, electronic, hydraulic and the like, with sliding or rotational action. Valve injectors having rotational action are preferred.

For improved precision it is preferred that all pumps be pulse-free and capable of very steady flow rate, e.g., high precision liquid chromatagraph pumps, and that all conduits, channels, valve ports and, of course, the capillary tube, be of narrow bore, preferably about 0.5 mm; connecting fittings should be zero dead volume fittings, and the analytical detector(s), typically of the flow-through type, should be equipped with a low volume flow cell.

The term "immiscible" herein refers to the art recognized qualitative classification applied to a pair of liquids tested by shaking together 5 ml. of the two liquids in a test tube for one minute, then allowing the mixture to settle. If an interfacial meniscus is present the liquids are deemed immiscible, even though some liquid pairs may exhibit some degree of partial miscibility, or reaction. Exemplary are polar and/or hydrophyllic liquids, such as water and aqueous acid, base and salt solutions, glycerol, diethanolamine and the like, which are immiscible with non-polar and/or hydrophobic liquids such as many organic volatile and non-volatile liquids, e.g., hydrocarbons such as propylene, benzene, and the like. Organic solvent pairs may be miscible or immiscible as exemplified in the CRC Handbook of Chemistry and Physics, 65th Ed. pp. C 702-704.

Each of the first and second liquids employed in the present system may be used in neat, i.e., pure form, or either one or both may have one or more reagents incorporated therein, as desired. Either the first or second liquid may be, e.g., hydrophyllic or hydrophobic, as desired.

What is claimed is:

1. Apparatus for measuring a property of a first liquid by extracting a component thereof from said first liquid into a second liquid which is a solvent for a component of said first liquid and is immiscible with said first liquid, separating a portion of said second liquid, and measuring a property of the component extracted into said second liquid, which apparatus comprises:

(a) first means for supplying, for supplying said first liquid from a source thereof to a first liquid flow system and at a substantially constant flow rate when said apparatus is in operation;

(b) said first liquid flow system comprising (1) a first multiport valve injector having a plurality of ports including a first inlet port in fluid communication with said first means for supplying, and a first outlet port in interruptible flow communication with said first inlet port and provided with fluid channels adapted to register with the aforesaid ports to control the flow of fluid through each said port, (2) extraction means for partitioning of a component from said first liquid into said second liquid and comprising capillary tubing configured to enhance mixing within the liquids passing therethrough; said tubing having two ends, an upstream end in flow communication with said first outlet port on said first valve injector and serving as an inlet, and a downstream end serving as an outlet, (3) a second multiport valve injector having a plurality of ports including a first inlet port in flow communication with said outlet end of said extraction means and having a first outlet port in interruptible flow communication with said first inlet port of said second valve injector and serving as an outlet of said first flow system; having liquid channels adapted to register with the aforesaid multiports to control the flow of liquid through each said port, and provided with means for injecting a fixed volume of the flow therethrough into a second liquid flow system;

(c) means for supplying second liquid immiscible with said first liquid from a source thereof into said second liquid flow system and at a substantially constant flow rate when said apparatus is in operation;

(d) said second liquid flow system comprising: (1) said second multiport valve injector having a second inlet port communicating with said means for supplying second liquid; having a second outlet port for passing said second liquid flow via conduit means downstream to property measurement means, and having flow injection means for discontinuously capturing a portion of substantially only said injected segment of second liquid from said first liquid flow system and injecting said portion into said second liquid flow system; and (2) said first multiport valve injector having a second inlet port communicating with means for suplying second liquid; having a second outlet port for passing said second liquid flow; and having flow injection means for discontinuously injecting a segment of said second liquid into said first flow system upstream of said extraction means;

(e) property measurement means coupled to said second liquid flow system downstream of said second valve injector, for measuring the desired property of the liquid flowing in said second liquid flow system;

(f) timing means coupled to said first valve injector to timely operate said first valve injector to periodically inject a segment of said second liquid into said first liquid flow system, and (g) activating means to timely operate said second valve injector to capture a portion of said segment of second liquid from said first liquid flow system after contact with the first liquid in said extraction means, and to inject said captured portion into said second fluid flow system.

2. The apparatus of claim 1 wherein said property measurement means is a flow through detector.

3. The apparatus of claim 1 wherein said property measurement means communicated with both said second means for supplying and to the flow of second liquid from said second valve injector to enable comparison of a measured property of the second liquid which has not extracted a component from said first liquid, as well a said property of second liquid after extraction of said first liquid.

4. The apparatus of claim 1 wherein said sequence timing means comprises: (1) means to timely operate said first valve injector to inject a segment of second liquid into said first liquid flow system, and (2) means for detecting second liquid detector means disposed at the downstream end of extraction means to detect the presence of the segment of injected second liquid and coupled to operate said second valve injector to capture a portion of said segment and to inject said portion into the second liquid flow system.

5. Apparatus for measuring a property of a first liquid by extracting a component thereof from said first liquid into a second liquid which is a solvent for a component of said first liquid and is immiscible with said first liquid, separating a portion of said second liquid, and measuring a property of the component extracted into said second liquid, which apparatus comprises:

(a) first means for supplying, for supplying said first liquid from a source thereof to a first liquid flow system and at a substantially constant flow rate when said apparatus is in operation;

(b) said first liquid flow system comprising (1) a first multiport valve injector having a plurality of ports including a first inlet port in fluid communication with said first means for supplying, and a first outlet port in interruptible flow communication with said first inlet port and provided with fluid channels adapted to register with the aforesaid ports to control the flow of fluid through each said port, (2) extraction means for partitioning of a component from said first liquid into said second liquid and comprising capillary tubing configured to enhance mixing within the liquids passing therethrough; said tubing having two ends, an upstream end in flow communication with said second port on said first valve injector and serving as an inlet, and a downstream end serving as an outlet, (3) a second multiport valve injector having a plurality of ports including a second inlet port in flow communication with said outlet end of said extraction means and having a second outlet port in interruptible flow communication with said second inlet port of said second valve injector and serving as an outlet of said first liquid flow system, having liquid channels adapted to register with the aforesaid multiports to control the flow of liquid through each said port and provided with means for injecting a fixed volume of the flow therethrough into said second liquid flow system;

(c) second means for supplying, for supplying a second liquid immiscible with said first liquid from a source thereof into a first part of second liquid flow system and at a substantially constant flow rate when said apparatus is in operation;

(d) said first part of said second liquid flow system comprising (1) said first multiport injector valve having a second inlet port communicating with said second means for supplying; having a second outlet port for passing said second liquid flow; and having flow injection means for discontinuously injecting a segment of said second liquid into said first liquid flow system upstream of said extraction means;

(e) third means for supplying, for supplying substantially second liquid from a source thereof, into a second part of second liquid flow system and at a substantially constant flow rate when said apparatus is in operation;

(f) said second part of second liquid flow system comprising: (1) said second multiport valve injector having a second inlet port communicating with said third means for supplying; having a second outlet port for passing said second liquid flow via conduit means downstream to property measurement means, and having flow injection means for discontinuously capturing a portion of substantially only said injected segment of second liquid from said first liquid flow system and injecting said portion into said second liquid flow system;

(g) property measurement means coupled to said second liquid flow system downstream of said second valve injector, for measuring the desired property of the liquid flowing in said second liquid flow system;

(h) timing means coupled to said first valve injector to timely operate said first valve injector to periodically inject a segment of said second liquid into said first liquid flow system, and
(i) activating means to timely operate said second valve injector to capture a portion of said previously injected segment of second liquid from said first liquid flow system after contact with the first liquid in said extraction means, and to inject said captured portion into said second fluid flow system.

6. The apparatus of claim 5 wherein said property measurement means is a flow through detector.

7. The apparatus of claim 5 wherein said property measurement means communicates with both said third means for supplying liquid and with the flow of second liquid from said second valve injector to enable comparison of a measured property of the second fluid which has not extracted a component from said first liquid, as well a said property of second liquid after extraction of said first liquid.

8. The apparatus of claim 5 wherein said sequence timing means comprises: (1) means to timely operate said first valve injector to inject a segment of second liquid into said first liquid flow system, and (2) means for detecting second liquid disposed at the downstream end of extraction means to detect the passage of the segment of injected second liquid, and coupled to operate said second valve injector to capture a portion of said previously injected segment and to inject said portion into the second liquid flow system.

* * * * *